(12) United States Patent
Reevell (10) Patent No.: US 10,743,587 B2
(45) Date of Patent: Aug. 18, 2020

(54) AEROSOL-GENERATING DEVICES AND AEROSOL-GENERATING SYSTEMS

(71) Applicant: Tony Reevell, London (GB)

(72) Inventor: Tony Reevell, London (GB)

(73) Assignee: Altria Client Services LLC, Richmond, VA (US)

( * ) Notice: Subject to any disclaimer, the term of this patent is extended or adjusted under 35 U.S.C. 154(b) by 164 days.

(21) Appl. No.: 15/922,085

(22) Filed: Mar. 15, 2018

(65) Prior Publication Data

US 2018/0263286 A1 Sep. 20, 2018

Related U.S. Application Data

(63) Continuation of application No. PCT/EP2018/055843, filed on Mar. 8, 2018.

(30) Foreign Application Priority Data

Mar. 16, 2017 (EP) .................................. 17161351

(51) Int. Cl.
*A24F 47/00* (2020.01)
*B01F 3/04* (2006.01)
(Continued)

(52) U.S. Cl.
CPC ......... *A24F 47/008* (2013.01); *A61M 11/003* (2014.02); *A61M 11/042* (2014.02);
(Continued)

(58) Field of Classification Search
CPC ....... A24F 47/008; B01F 3/04; B01F 3/04007
See application file for complete search history.

(56) References Cited

U.S. PATENT DOCUMENTS

2012/0048266 A1 3/2012 Alelov
2013/0014772 A1 1/2013 Liu
(Continued)

FOREIGN PATENT DOCUMENTS

CN 203378558 U 1/2014
EP 2989912 A1 * 3/2016 ........... A24F 47/008
(Continued)

OTHER PUBLICATIONS

International Preliminary Report on Patentability dated Sep. 26, 2019 for corresponding International Application No. PCT/EP2018/055843.
(Continued)

*Primary Examiner* — Robert A Hopkins
(74) *Attorney, Agent, or Firm* — Harness, Dickey & Pierce, P.L.C.

(57) ABSTRACT

An aerosol-generating system includes an aerosol-generating device and at least two consumables. Each consumable includes an aerosol-forming substrate. The aerosol-generating device further includes a device housing comprising at least two receiving chambers, wherein each consumable is accommodated in a separate receiving chamber of the at least two receiving chambers. The aerosol-generating device further includes at least two mouthpieces, wherein each mouthpiece of the at least two mouthpieces is aligned with a separate consumable of the at least two consumables and wherein the aerosol-generating device is configured to isolate airflows through separate, respective mouthpieces of the at least two mouthpieces.

19 Claims, 4 Drawing Sheets

(51) Int. Cl.
  *A61M 15/06* (2006.01)
  *A61M 15/00* (2006.01)
  *A61M 11/00* (2006.01)
  *A61M 11/04* (2006.01)
  *B01F 3/02* (2006.01)
  *G05B 15/02* (2006.01)

(52) U.S. Cl.
  CPC .... *A61M 15/0003* (2014.02); *A61M 15/0021* (2014.02); *A61M 15/0026* (2014.02); *A61M 15/06* (2013.01); *B01F 3/022* (2013.01); *B01F 3/04007* (2013.01); *B01F 3/0407* (2013.01); *G05B 15/02* (2013.01); *A61M 2205/3653* (2013.01)

(56) References Cited

U.S. PATENT DOCUMENTS

2013/0333700 A1    12/2013  Buchberger
2014/0060556 A1    3/2014   Liu
2016/0324212 A1    11/2016  Cameron

FOREIGN PATENT DOCUMENTS

WO    WO-2013/152873 A1    10/2013
WO    WO-2015/179388 A1    11/2015
WO    WO-2019122878 A1 *   6/2019    ........... A24F 47/008

OTHER PUBLICATIONS

"The Next Generation Hybrid Vaping and New Way to Consume Tobacco" Jinjia Technologies.

M. Geller "British American to test tobacco/e-cigarette hybrid" Reuters, last accessed: Nov. 14, 2017.

Extended European Search Report for European Patent application No. 17161351.6 dated Sep. 15, 2017.

* cited by examiner

AEROSOL-GENERATING DEVICES AND AEROSOL-GENERATING SYSTEMS

CROSS-REFERENCE TO RELATED APPLICATIONS

This application is a continuation of, and claims priority to, international application no. PCT/EP2018/055843, filed on Mar. 8, 2018, and further claims priority under 35 U.S.C. § 119 to European Patent Application No. 17161351.6, filed on Mar. 16, 2017, the entire contents of each of which are incorporated herein by reference.

BACKGROUND

Field

Some example embodiments relate to aerosol-generating devices, (also called vapor-generating devices). In particular, some example embodiments relate to aerosol-generating devices suitable for being used with more than one consumable, in particular with different types of consumables.

Description of Related Art

Aerosol-generating devices (also called vapor-generating devices), including so-called electronic cigarettes, are known to use a liquid to be evaporated or tobacco material to be heated. In some devices, the evaporation of a liquid is combined with heating tobacco. In other devices, two reservoirs comprising different liquids are provided for selective parallel evaporation of the different liquids.

SUMMARY

According to some example embodiments, an aerosol-generating system may include an aerosol-generating device. The aerosol-generating device may include a device housing, the device housing including at least two receiving chambers. The aerosol-generating device may include at least two consumables including an aerosol-forming substrate, each consumable of the at least two consumables accommodated in a separate receiving chamber of the at least two receiving chambers. The aerosol-generating device may include at least two mouthpieces, each mouthpiece of the at least two mouthpieces aligned with a separate consumable of the at least two consumables. The aerosol-generating device may be configured to isolate airflows through separate, respective mouthpieces of the at least two mouthpieces.

At least one mouthpiece of the at least two mouthpieces may be included in the aerosol-generating device.

The aerosol-generating device may include a mouthpiece assembly, the mouthpiece assembly including the at least two mouthpieces.

At least one consumable of the at least two consumables may include one mouthpiece of the at least two mouthpieces.

One consumable of the at least two consumables may include an aerosol-forming liquid and a heating element, the heating element configured to heat the aerosol-forming liquid.

One consumable of the at least two consumables may include a solid tobacco material.

The aerosol-generating device may be a handheld device.

According to some example embodiments, an aerosol-generating device may include a device housing including at least two receiving chambers. Each receiving chamber of the at least two receiving chambers may be configured to receive and accommodate a separate consumable. Each receiving chamber of the at least two receiving chambers may include one of a heating element configured to heat a consumable accommodated in the receiving chamber, electrical contacts connectable to an external heating element of a consumable, the electrical contacts configured to heat the consumable accommodated in the respective receiving chamber, or an induction coil configured to heat a susceptor material provided in the aerosol-generating device or in the consumable.

The aerosol-generating device may further include at least two mouthpieces, wherein each mouthpiece of the at least two mouthpieces covers a receiving opening of a receiving chamber of the at least two receiving chambers based on the mouthpiece being mounted to the device housing.

Each mouthpiece may be connected to the device housing via a hinge.

Each mouthpiece of the at least two mouthpieces may include an inlet opening and an mouthpiece opening, and each inlet opening may be aligned with a receiving opening of a separate receiving chamber of the at least two receiving chambers.

The aerosol-generating device may be configured to isolate airflows through separate, respective mouthpieces of the at least two mouthpieces.

The aerosol-generating device may further include a mouthpiece assembly that includes at least two mouthpieces.

At least one receiving chamber of the at least two receiving chambers may include a heating element, and the heating element may be in a receiving chamber wall or extend into the at least one receiving chamber.

Each receiving chamber may be elongate and have a longitudinal axis, and the at least two receiving chambers may extend in parallel in the device housing such that the longitudinal axes of the at least two receiving chambers extend in parallel.

Each receiving chamber may be elongate and have a longitudinal axis, and the longitudinal axes of the at least two receiving chambers may extend in different directions within the device housing.

The device housing may include three or more receiving chambers configured to receive and accommodate three or more consumables.

Each receiving chamber may be elongate and have a longitudinal axis, and the longitudinal axes of the three or more receiving chambers may extend in different directions and the longitudinal axes of adjacent receiving chambers may intersect at an alignment angle, the alignment angles between the longitudinal axes of all of the adjacent receiving chambers being substantially equal.

The aerosol-generating device may be a handheld device.

BRIEF DESCRIPTION OF THE DRAWINGS

Example Embodiments are further described with regard to the following drawings, wherein.

In the figures the same reference numbers are used for the same or similar elements.

DETAILED DESCRIPTION

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, and/or elements, but do not preclude the presence or addition of one or more other features, integers, steps, operations, elements, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, regions, layers and/or sections, these elements, regions, layers and/or sections should not be limited by these terms. These terms are only used to distinguish one element, region, layer or section from another region, layer or section. Thus, a first element, region, layer or section discussed below could be termed a second element, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Some example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

When the terms "about" or "substantially" are used in this specification in connection with a numerical value, it is intended that the associated numerical value include a tolerance of ±10% around the stated numerical value. The expression "up to" includes amounts of zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure.

According to some example embodiments there is provided an aerosol-generating device (also called a vapor-generating device). The device comprises a device housing comprising at least two receiving chambers for receiving and accommodating ("configured to receive and accommodate") a consumable in each one of the at least two receiving chambers.

In some example embodiments, each receiving chamber of the at least two receiving chambers may comprise one of a heating element configured to heat a consumable accommodated in the respective receiving chamber or electrical contacts connectable to an external heating element of a consumable, where the external heating element is configured to heat the consumable accommodated in the respective receiving chamber, or an induction coil configured to heat a susceptor material provided in the device or in the consumable.

The device may further comprise at least two mouthpieces, wherein each mouthpiece of the at least two mouthpieces, in response to being mounted to the device housing, cover a receiving opening of a receiving chamber of the at least two receiving chambers.

An airflow into and out of each mouthpiece of the at least two mouthpieces may be kept separate from the airflow into and out of each of the other of the at least two mouthpieces. Restated, the aerosol-generating device may isolate airflows through separate, respective mouthpieces of the at least two mouthpieces.

With this device, each receiving chamber is accessible via a separate mouthpiece. Thus, each consumable arranged in the receiving chambers is accessible via a separate mouthpiece. At least two, preferably different, consumables may be accommodated in the device and are then in a state ready to be used by a user (also called an adult vaper) without further preparation of the device. For example, no repositioning of a mouthpiece is required if one of the consumables is selected for being used. In particular, a switching between different consumables, for example between subsequent puffs (e.g., between separate draws of air through an airflow path of the aerosol-generating device via one or more mouthpieces by an adult vaper), is readily available. In addition, different receiving chambers and respective mouthpieces may individually be used only for specific types of consumables. The assignment of one mouthpiece to one receiving chamber prevents contamination of a receiving chamber and respective mouthpiece with substances from a consumable accommodated in another receiving chamber. This may enhance a sensory experience provided by the device over a longer period of use of the device.

The aerosol-generating device provides an adult vaper with the choice which consumable accommodated in the receiving chamber shall be used, subsequently or alternatingly and to what extent. Depending on the type ("kind") of consumables provided in the receiving chambers a desired consumer experience may be selected spontaneously. For example, a spontaneous selection may be made between a flavor-based experience or a nicotine-based experience.

In some example embodiments, each mouthpiece of the at least two mouthpieces comprises an inlet opening and an outlet opening. Each of the inlet openings are aligned with a receiving opening of one of the at least two receiving chambers, and thus may be aligned with a separate consumable of at least two consumables accommodated in separate receiving chambers of at least two receiving chambers. Each of the outlet openings are individually accessible by an adult vaper. Thus, puffing (e.g., drawing air through at least one airflow pathway from an inlet opening to an outlet opening and through an aerosol-generating device) at any of the mouthpieces is available anytime. Depending on the consumable accommodated in the receiving chamber associated with the respective mouthpiece the adult vaper is drawing air through the aerosol-generating device at, a respective sensory experience is provided.

The mouthpieces may be separate, independent device parts. This enables each receiving chamber to be opened and closed separately ("independently"), for example for a removal or replacement of a consumable.

The mouthpieces may form a mouthpiece unit (also called a mouthpiece assembly). Restated, an aerosol-generating device may include a mouthpiece assembly that includes at least two mouthpieces. Thus, the at least two mouthpieces may be connected, for example integrated into an assembly of mouthpieces. By this only one device part needs to be manufactured and assembled with a device housing. In addition only one device part needs to be handled to gain access to all receiving chambers of the device at a same time.

A device may comprise mouthpieces all being separate device parts. A device may comprise mouthpieces being separate device parts and a mouthpiece assembly. A device may comprise one or more mouthpiece assemblies. For example, a device may comprise a mouthpiece assembly, for example, comprising two connected mouthpieces and one or more individual mouthpieces. A device may, for example also comprise two mouthpiece assemblies, each comprising for example two connected mouthpieces.

In some example embodiments, the at least two mouthpieces of the device may form a mouthpiece assembly. Advantageously, an airflow into and out of each of the at least two mouthpieces of the mouthpiece assembly may be kept separate for each of the at least two mouthpieces. By this, a mixing of evaporated substances from two or more consumables may be kept separate although the mouthpieces are assembled in one device part.

Substances from a substrate contained in the consumable may be transported by an airflow passing through the substrate or through the consumable, respectively. These substances may simply be entrained by the passing airflow. For example, an airflow passing a tobacco substrate may be entrained with tobacco flavor. The substances to be entrained may also actively be generated, for example, by heating a substrate contained in the consumable and forming an aerosol (also called a vapor). Also other atomization processes may be used for aerosol generation.

In the device, preferably, at least one of the at least two consumables is heatable.

In the device, all consumables may be heatable.

Advantageously, for aerosolization (also called or including vaporization) of a consumable or of substances comprised in the consumable, the substrate is heated. This may be done by heating the substrate via heating element in the consumable or by providing a heating element in the device. If a heating element or another atomization element is comprised in the consumable itself, a receiving chamber preferably comprises respective electrical contacts for connecting an electrical power source in the device to the consumable for providing the required power to the atomization element, for example heater, in the consumable.

Heating of a consumable is preferably performed resistively or inductively. A resistively heatable heating element may be provided in the device or in the consumable. With inductive heating, an inductor, for example an induction coil, is preferably provided in the device. A susceptor material heated by the inductor may be provided in the device or in the consumable.

Preferably, at least one receiving chamber of the at least two receiving chambers comprises a heating element for heating a consumable accommodated in the respective receiving chamber or comprises electrical contacts connectable to an external heating element of a consumable for heating the consumable accommodated in the respective receiving chamber.

One receiving chamber may comprise a heating element and another receiving chamber may comprise electrical contacts.

Both of the at least two receiving chambers may comprise both, a heating element and electrical contacts for example for an external atomization element. This provides many options for different consumables to be included in the aerosol-generating device according to some example embodiments. This also facilitates use of the device by not having to check if a receiving chamber is adapted for a specific consumable or aerosolization option.

A heating element in the device may be arranged in a receiving chamber wall. For example resistively heatable metal tracks may be arranged at a receiving chamber wall or resistively heatable wires may be arranged in the receiving chamber wall. An inductor in the form of an induction coil may be arranged in a receiving chamber wall and surround a consumable accommodated in the receiving chamber.

A heating element in the device may extend into a receiving chamber. For example, the heating element may be a resistively heated heater blade or an elongated susceptor. At least one of the receiving chambers may comprise a heating element extending into the receiving chamber.

Various types of consumables may be used or may be determined to be usable with the aerosol-generating device according to some example embodiments.

Examples of consumables are, for example, but not limited to: liquid containing cartridges (also called reservoirs) or tank systems including or excluding an integrated aerosolization element (also referred to as an integrated vaporizer assembly) such as for example cartomizers (also called cartridges, a combined reservoir and atomizer); solid substrate containing consumables such as for example tobacco containing plugs; solid substrate containing capsules, wherein the solid substrate may be tobacco material, homogenized tobacco material or substrate in powder form; vaporizable wax; tobacco sheets that are gathered or crimped.

In some example embodiments, a tobacco material may include material from any member of the genus *Nicotiana*. In some example embodiments, the tobacco material includes a blend of two or more different tobacco varieties. Examples of suitable types of tobacco materials that may be used include, but are not limited to, flue-cured tobacco, Burley tobacco, Maryland tobacco, Oriental tobacco, rare tobacco, specialty tobacco, dark tobacco, blends thereof and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass.

The receiving chambers may accommodate different types of consumables, for example a liquid containing reservoir and a solid substrate containing consumable, preferably a solid tobacco substrate containing consumable.

Different consumables may differ in shape, for example, in a diameter. Preferably, different consumables contain any one or a combination of different aerosol-forming substrate (also called a vapor-forming substrate), for example different tobacco material, different flavor, different nicotine content, different substance combination. Preferably, different consumables comprise a different way of being heated or in general a different way the substance of the consumable is atomized. Different consumables may comprise both different aerosol-forming substrate and a different way of atomizing the substrate.

The receiving chambers may comprise consumables of a same kind, for example liquid containing reservoirs. Preferably, the reservoirs then contain a different liquid, for example having different flavor or different substance combination.

The consumables may make use of different methods for releasing substances from the consumables. For example, when one consumable in one receiving chamber comprises a heatable liquid, another consumable in another receiving chamber may be a non-heated tobacco substrate or may contain a non-heated but otherwise atomized substrate.

Preferably, the at least two receiving chambers are arranged parallel and next to each other in the device housing. Preferably the at least two receiving chambers are arranged in a line next to each other. The receiving chambers may also be arranged in a closed packed manner. For example, three receiving chambers may be arranged in a triangle or four receiving chambers may be arranged in the form of a parallelepiped.

In some example embodiments, each receiving chamber may be elongate and have a longitudinal axis. The at least two receiving chambers may be arranged next to each other in the device housing with their longitudinal axes in parallel.

'Arranged parallel' is herein meant that a longitudinal axis of the receiving chambers is arranged parallel. The longitudinal axis is typically arranged along an insertion direction of a consumable into the receiving chamber. Receiving chambers arranged parallel and next to each other have their receiving openings directing in a same direction such that the receiving chambers may be filled from a same, for example top, direction.

In some example embodiments, each receiving chamber is elongate and has a longitudinal axis and the at least two receiving chambers are arranged in the device housing such that the longitudinal axes of the at least two receiving chambers extend in different directions. In other words, the at least two receiving chambers may be arranged such that their longitudinal axes are not in parallel. The at least two receiving chambers may be arranged in the device housing such that the longitudinal axis of the at least two receiving chambers include an alignment angle. The alignment angle is larger than 0 degree.

An alignment angle may be the same or may be different between neighboring receiving chambers. Thus, receiving chambers may be arranged symmetrically or asymmetrically in the device housing.

Preferably, an alignment angle is the same between all receiving chambers in the device.

Preferably, an alignment angle is between 30 degree and 180 degree for two receiving chambers, for example between 45 degree and 90 degree. An alignment angle of 180 degree with two receiving chambers corresponds to an opposite arrangement (opposite insertion directions) of the two receiving chambers in the device housing.

In some example embodiments, the device comprises three or more receiving chambers configured to accommodate three or more consumables. Preferably, three receiving chambers are arranged such as to include an alignment angle of between 30 degree and 150 degree. Preferably, three receiving chambers are arranged such as to include an alignment angle of 120 degree between neighboring receiving chambers.

The receiving chambers may be arranged in a same plane. The receiving chambers may be arranged in different planes, for example in planes parallel to each other or in a cone-shaped manner.

Preferably, all receiving chambers lie in one plane.

Preferably, the device comprises two or three mouthpieces and the device housing comprises two or three receiving chambers for receiving and accommodating two or three consumables.

Preferably, the three or more receiving chambers are arranged in a star-like manner in the device housing.

In some example embodiments, each receiving chamber is elongate and has a longitudinal axis and the longitudinal axes of the three or more receiving chambers extend in different directions. The longitudinal axes of adjacent or neighboring receiving chambers may intersect at an alignment angle, wherein the alignment angles between the longitudinal axes of all of the adjacent or neighboring receiving chambers being substantially similar or equal.

Preferably, the proximal ends of the at least two receiving chambers or the receiving openings of the at least two receiving chambers are arranged flush with a top or with an outer circumference of the device housing. If the receiving chambers are all arranged next to each other in one line then the receiving openings of the receiving chambers are preferably arranged flush with a top of the device housing. If the receiving chambers are arranged including an alignment angle in between neighboring receiving chambers, then the receiving openings of the receiving chambers are preferably arranged flush with a circumference of the device housing.

Mouthpieces may be removably connected to the device housing.

Mouthpieces may be completely disassembled or may only partly be removed from the housing for gaining access to the receiving chambers. Mouthpieces may be connected to the device housing, for example, in a hinged manner (e.g., via a hinge).

Preferably, each mouthpiece is connected to the device housing in a hinged manner. Thereby, each mouthpiece is individually connected to the device housing by a separate hinge. All or some of the mouthpieces may also form a mouthpiece assembly, which assembly is connected to the device housing in a hinged manner. Depending on the construction of the mouthpiece assembly, one or more hinges may be provided.

The consumables may partially or entirely be inserted into a receiving chamber. A partial insertion facilitates the removal of the consumable after use. Thereby, an adult vaper may grip an extending portion of the consumable.

Removal of a consumable from a receiving chamber may also be facilitated by the provision of cutouts in the device housing that enable a gripping of the consumable. Preferably, two oppositely arranged cutouts are provided in a receiving chamber.

The device housing may be provided with cutouts in an opening portion of a receiving chamber.

All opening portions of all receiving chambers in the device may be provided with cutouts.

The device may be a portable device. Preferably, the device is a handheld device. In other words, the device may be a portable device that is configured to be held in the hand of an adult vaper during use. The device housing may be sized and shaped to enable an adult vaper to hold the device in a hand during use.

According to some example embodiments there is further provided an aerosol-generating system (also called a vapor-generating system) comprising an aerosol-generating device and at least two consumables comprising an aerosol-forming substrate. The device comprises a device housing comprising at least two receiving chambers, wherein each of the at least two consumables is accommodated in one of the at least two receiving chambers. The system further comprises at least two mouthpieces, wherein each of the at least two mouthpieces is aligned with one of the at least two consumables.

An airflow into and out of each of the at least two mouthpieces may be kept separate from the airflow into and out of each of the other of the at least two mouthpieces.

Advantages of a system wherein two or more consumables are ready for being used, and wherein individual mouthpieces are assigned to each of the consumables have been described relating to the aerosol-generating device and will not be repeated.

Preferably, the at least two consumables are different consumables.

Preferably, one of the at least two consumables comprises aerosol-forming liquid (also called vapor-forming liquid) and a heating element for heating the aerosol-forming liquid.

Preferably, one of the at least two consumables comprises solid tobacco material.

At least one of the at least two mouthpieces of the system may be comprised in the device. The at least two mouthpieces of the system may be comprised in the device. At least one of the at least two mouthpieces of the system may be comprised in at least one of the at least two consumables. The at least two mouthpieces of the system may be comprised in at least two consumables.

A mouthpiece comprised in a consumable is arranged at a proximal end of the consumable. Preferably, a mouthpiece comprised in the consumable forms an end stop. The end stop prevents the consumable from being further inserted into a receiving chamber. An end stop may also make sure that the mouthpiece is arranged outside of the receiving chamber.

Preferably, a mouthpiece of a consumable comprises an outlet opening. Preferably, the outlet opening is centrally arranged in the mouthpiece. Preferably, mouthpieces of consumables are arranged flush with a device housing wall when the consumable is accommodated in the receiving chamber of the device housing.

Preferably, the at least two mouthpieces are comprised in the device.

Preferably, the aerosol-generating device of the system is an aerosol-generating device according to some example embodiments and as described herein.

The at least two mouthpieces may form a mouthpiece assembly, wherein an airflow into and out of each of the at least two mouthpieces is kept separate for each of the at least two mouthpieces in the mouthpiece assembly.

According to some example embodiments, there is also provided an aerosol-generating device comprising a device housing comprising at least two receiving chambers for receiving and accommodating a consumable in each one of the at least two receiving chambers, wherein the at least two receiving chambers are arranged in the device housing such that the longitudinal axis of the at least two receiving chambers include an alignment angle. The alignment angle is larger than 0 degree.

The receiving chambers may be arranged symmetrically or asymmetrically in the device housing. An alignment angle may be the same or may be different between neighboring receiving chambers, in particular if more than two receiving chambers are arranged in the device housing.

Preferably, an alignment angle is the same between all receiving chambers in the device.

Preferably, an alignment angle is between 30 degree and 180 degree for two receiving chambers, for example between 45 degree and 90 degree. An alignment angle of 180 degree with two receiving chambers corresponds to an opposite arrangement (opposite insertion directions) of the two receiving chambers in the device housing.

Preferably, three receiving chambers are arranged such as to include an alignment angle of between 30 degree and 150 degree. Preferably, three receiving chambers are arranged such as to include an alignment angle of 120 degree between neighboring receiving chambers.

The receiving chambers may be arranged in a same plane. The receiving chambers may be arranged in different planes, for example in planes parallel to each other or in a cone-shaped manner.

Preferably, all receiving chambers lie in one plane.

Preferably, three or more receiving chambers are arranged in a star-like manner in the device housing.

Preferably, the proximal ends of the at least two receiving chambers or the receiving openings of the at least two receiving chambers are arranged flush with a top or with an outer circumference of the device housing. The receiving openings of the receiving chambers are preferably arranged flush with a circumference of the device housing.

The device may further comprise at least two mouthpieces, wherein each of the at least two mouthpieces when mounted to the device housing cover a receiving opening of a receiving chamber of the at least two receiving chambers.

Preferably, the device comprises two or three mouthpieces and the device housing comprises two or three receiving chambers for receiving and accommodating two or three consumables.

Preferably, the each of the at least two receiving chambers is provided with a separate independent mouthpiece. However, depending on a distance between the at least two receiving chambers, the mouthpieces may for a mouthpiece assembly.

The device of the system may be a portable device. Preferably, the device is a handheld device. In other words, the device may be a portable device that is configured to be held in the hand of an adult vaper during use. The device housing may be sized and shaped to enable an adult vaper to hold the device in a hand during use.

Figure 1:
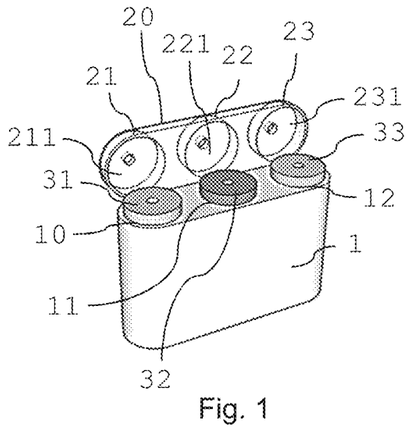
FIGS. 1 and 2 show perspective views of an aerosol-generating device comprising three consumables with a mouthpiece assembly in an open and closed state, according to some example embodiments.
Figure 2:
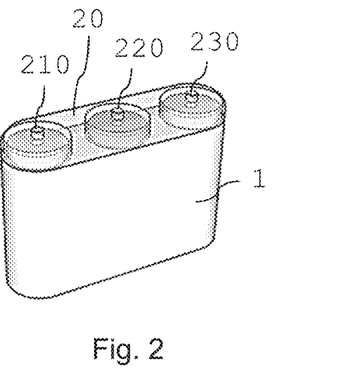

FIGS. 1 and 2 show perspective views of an aerosol-generating device comprising three consumables with a mouthpiece assembly in an open and closed state, according to some example embodiments.

The aerosol-generating device shown in FIG. 1 and FIG. 2 comprise a device housing 1 and a mouthpiece assembly 20 in an open and a closed state. The mouthpiece assembly 20 is connected to the device housing with a hinge.

The device housing 1 comprises three tubular shaped receiving chambers 10, 11, 12 accommodating three consumables 31, 32, 33. The consumables are tubular shaped and slightly extend out of the receiving chambers 10, 11, 12 when accommodated therein.

The three consumables are arranged parallel next to each other and in one line in the device housing 1. The device housing and the mouthpiece assembly 20 basically have a rectangular shape with rounded edges.

Preferably, the size of the housing 1 and of the mouthpiece assembly 20 is selected to the sizes of the three consumables 31, 32, 33 as well as to allow individual draws of air on each of the consumables.

The mouthpiece assembly 20 covers all three consumables 31, 32, 33 or all three receiving chamber inlets, respectively.

The mouthpiece assembly 20 comprises three mouthpieces 21, 22, 23. Each mouthpiece 21, 22, 23 comprises an inlet opening 211, 221, 231 and an outlet opening 210, 220, 230. The inlet opening covers a consumable when the mouthpiece assembly is in the closed state as shown in FIG. 2.

The outlet openings 210, 220, 230 allow separate draws of air on each of the mouthpieces 21, 22, 23 of the mouthpiece assembly 20.

Preferably, the mouthpieces 21, 22, 23 of the mouthpiece assembly 20 close tightly around the consumables such that no airflow between neighboring consumables is mixed when drawing air at an outlet opening of one mouthpiece.

The mouthpiece assembly 20 of FIGS. 1 and 2 is made of a transparent material to allow view into the device and to the consumables accommodated in the device. The mouthpiece assembly 20 may also be non-transparent as the device housing shown in these figures.

Preferably, the consumables 31, 32, 33 are aerosol-generating articles comprising aerosol-forming substrate. Preferably, the consumables 31, 32, 33 are different types of consumables. A first consumable 31 may, for example, be a heatable aerosol-forming liquid containing reservoir, for example a cartridge where an atomization source is incorporated in the reservoir. The second consumable 32 may, for example, be a heatable tobacco material containing article and the third consumable may, for example be a non-heated solid tobacco material containing article.

Figure 3:
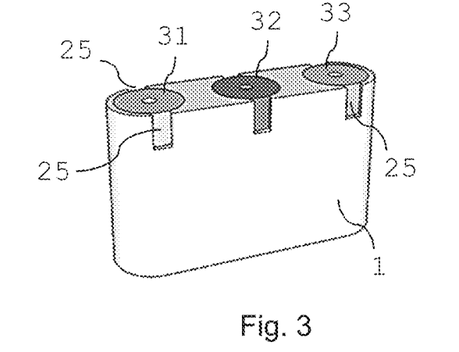
FIG. 3 shows a perspective view of an aerosol-generating device comprising cutouts for access to the consumables in the device, according to some example embodiments.

FIG. 3 shows a perspective view of an aerosol-generating device comprising cutouts for access to the consumables in the device, according to some example embodiments.

FIG. 3 shows a device housing 1 comprising three receiving chambers arranged in one line next to each other and parallel to each other. The three consumables 31, 32, 33 accommodated in the respective receiving chambers are completely inserted in the chambers such that the proximal ends of the consumables are arranged flush with the top of the device housing 1.

The receiving chamber walls of the receiving chambers each comprise two opposite and longitudinally arranged slits 25. The consumables 31, 32, 33 may be removed from the receiving chambers by gripping the consumable via the slits 25.

Figure 4:
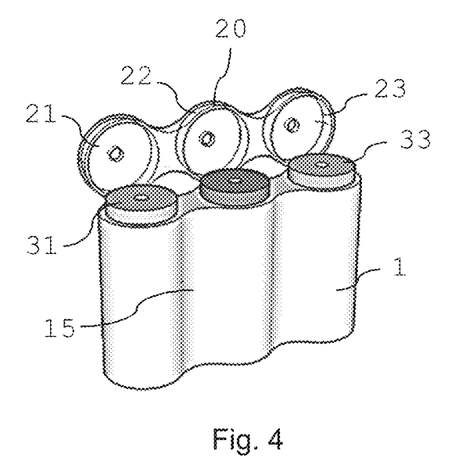
FIGS. 4 and 5 show perspective views of an ergonomically shaped aerosol-generating device comprising a mouthpiece assembly in an open and a closed state, according to some example embodiments.
Figure 5:
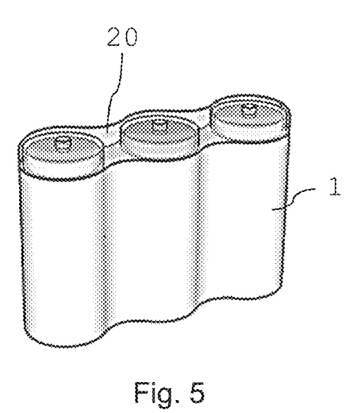

FIGS. 4 and 5 show perspective views of an ergonomically shaped aerosol-generating device comprising a mouthpiece assembly in an open and a closed state, according to some example embodiments.

The aerosol-generating device shown in FIG. 4 and FIG. 5 comprise a device housing 1 and a mouthpiece assembly 20 in an open and closed state. The mouthpiece assembly 20 is connected to the device housing 1 with three hinges.

The device is similar to the one shown in FIG. 1 and FIG. 2. However, the device housing 1 as well as the mouthpiece assembly 20 comprise a wave-like cross section. The device housing 1 comprises two longitudinal dents 15 in locations between the receiving chambers. The mouthpiece assembly 20 comprises bridges between neighboring mouthpieces 21, 22, 23 such that periphery of the mouthpiece assembly 20 is flush with the periphery of the device housing 1 when in a closed state. The form of the device housing 1 provides an ergonomic shape and may facilitate holding of the device. The device also has a reduced overall volume and special appearance.

Figure 6:
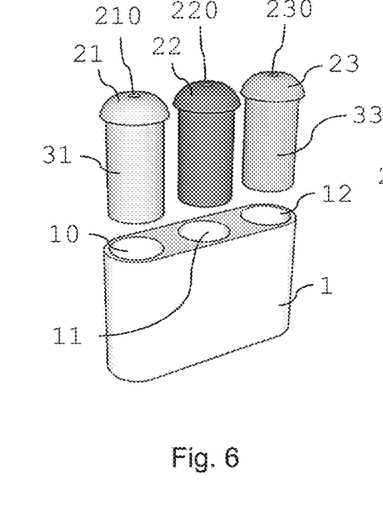
FIGS. 6 and 7 show perspective views of an aerosol-generating device comprising three consumables with integrated mouthpiece before and after insertion of the consumables, according to some example embodiments.
Figure 7:
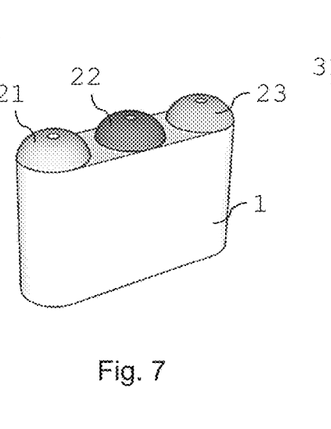

FIGS. 6 and 7 show perspective views of an aerosol-generating device comprising three consumables with integrated mouthpieces before and after insertion of the consumables, according to some example embodiments.

FIG. 6 and FIG. 7 show an aerosol-generating device, wherein the device housing 1 comprises three receiving chambers arranged in one line and parallel to each other. The device housing 1 may, for example, be the same as the device housing of FIG. 1.

In the example of FIGS. 6 and 7, the mouthpieces are integrated into the consumables 31, 32, 33. Each tubular shaped consumable 31, 32, 33 comprises a dome-shaped mouthpiece 21, 22, 23. The dome-shaped mouthpieces are arranged at the proximal ends of the consumables. The mouthpieces extend radially over the circumference of the consumable such as to form an end-stop. When inserted into the receiving chambers as shown in FIG. 7, the consumables are accommodated in the receiving chambers and the mouthpieces 21, 22, 23 extend from the receiving chamber. Each mouthpiece 21, 22, 23 comprises an outlet opening 210, 220, 230 through which an adult vaper may draw substances from the respective consumable.

The circumferences of the mouthpieces do not extend laterally over the edge of the device housing 1.

Figure 8:
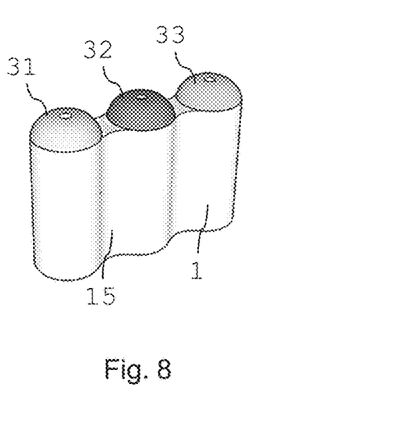
FIG. 8 shows the consumables of FIG. 7 inserted onto an ergonomically shaped device, according to some example embodiments.

FIG. 8 shows the consumables of FIG. 7 inserted onto an ergonomically shaped device, according to some example embodiments.

The device housing 1 shown in FIG. 8 comprises a wave-like cross section. The device housing 1 may, for example, be the same as the one shown in FIG. 5 comprising two longitudinal dents 15 in locations between the receiving chambers. Three consumables 31, 32, 33 comprising dome-shaped mouthpieces are accommodated in the receiving chambers. The combination of wave-shaped device housing 1 and dome-shaped mouthpieces basically forms three tubular assemblies that are combined in the device housing 1.

Figure 9:
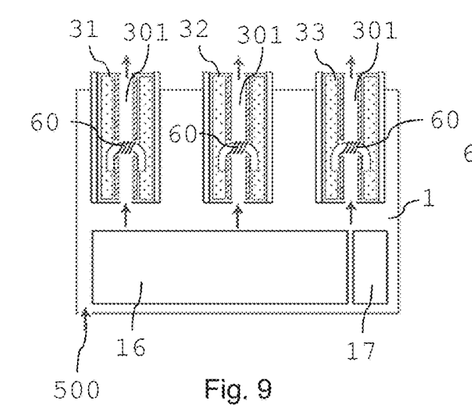
FIG. 9 shows a cross section through a device and an airflow through a common kind of consumables, according to some example embodiments.
Figure 10:
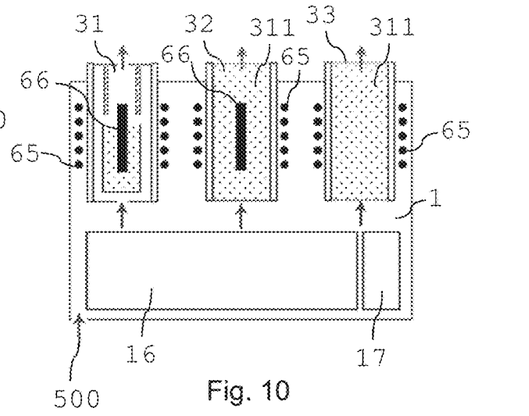
FIGS. 10 and 11 show a cross section through devices and airflow through different types of consumables, according to some example embodiments.
Figure 11:
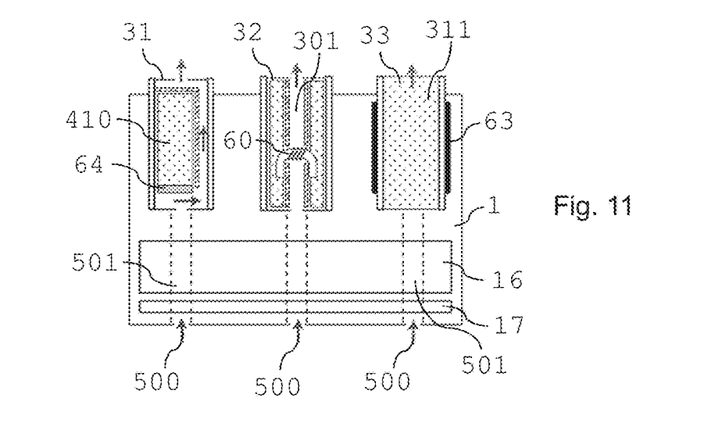

FIG. 9 shows a cross section through a device and an airflow through a common kind of consumables, according to some example embodiments. FIGS. 10 and 11 show a cross section through devices and airflow through different types of consumables, according to some example embodiments.

FIG. 9, FIG. 10 and FIG. 11 schematically show cross sections through aerosol-generating devices comprising three consumables arranged in parallel, for example embodiments of the devices as shown in FIGS. 1 to 8.

FIGS. 9 to 11 also show examples of airflows passing through the three consumables.

The device housing 1 comprise three receiving chambers (not shown) arranged in parallel, three consumables 31, 32, 33 accommodated in the receiving chambers, a power source 16 and a controller 17 for controlling the power source and the device.

In FIG. 9 the three consumables are of a same type. All three consumables are a heated liquid containing reservoir. An aerosol-forming liquid is contained in a hollow tubular shaped reservoir. The liquid is supplied by a wick material to a coil heater 60, where the liquid is heated and evaporated. In a central conduit 301 of the consumables, the evaporated liquid is led out of the receiving chamber.

The three cartridges preferably differ in terms of at least one of nicotine strength, flavor or vapor volume.

The receiving chambers comprise electrical contacts (not shown) for providing power from the power source 16 to the coil heater 60 of the consumables 31, 32, 33.

Preferably, the consumables 30, 31 are heated individually and only the one consumable an adult vaper is drawing on provides substances to an airflow 500 to be drawn by the adult vaper.

An airflow 500 enters the device through one opening at a distal end of the device (bottom wall), passes through the device housing 1 and may enter the distal end of a receiving chamber. The airflow 500 passes the receiving chamber and through the consumable accommodated in the receiving chamber. Thereby the airflow 500 picks up evaporated substances.

The airflow 500 may then pass through a mouthpiece (not shown), which is aligned with the respective consumable and receiving chamber.

The controller 17 of the device is configured to provide required power to a coil heater 60.

FIG. 10 shows an aerosol-generating device with a same airflow 500 management as described in FIG. 9 according to some example embodiments. The same reference numbers are used for the same or similar elements.

The device housing 1 schematically shown in FIG. 10 comprises induction heating.

In the receiving chamber side walls an induction coil 65 is arranged. Each induction coil 65 surrounds the respective receiving chamber.

The consumables 31, 32 arranged in the first and second receiving chamber comprise a susceptor 66, for example a ferrous material, for heating an aerosol-forming substrate in the consumable. The first consumable 31 of FIG. 10 is depicted as containing liquid that is wicked and evaporated by the heated susceptor. The second and third consumables of FIG. 10 are depicted as a shell, preferably tubular shaped, filled with a solid tobacco material 311, for example shredded tobacco or homogenized tobacco material. The tobacco material 311 of the second consumable 32 is heated by the susceptor 66 arranged in the tobacco material. The tobacco material 311 of the third consumable 33 is not heated. The airflow 500 passing through the third consumable 33 picks up substances, mainly flavor, from the non-heated tobacco material 311.

A detection system in the device may be integrated or connected to the controller 17 and may recognize the type of consumable accommodated in the receiving chambers. For example, next to an electronic recognition, a touch sensor may be provided in the receiving chamber for recognition of the presence or absence of a consumable.

In the device of FIG. 11, three different types of consumables are arranged in the device housing 1. A first consumable 31 comprises aerosol-forming liquid in a storage portion 410 of the consumable 31. The storage portion 410 comprises an open end, where a mesh heater 64 or other fluid permeable heater, is arranged over the open end. The liquid is heated by the heated mesh heater 64. The consumable is positioned in the receiving chamber 3 such that an airflow 500 entering the distal end of the receiving chamber 3 passes the mesh heater 64, thereby pick up evaporated substances, passes along the exterior of the storage portion 410 and out of the device housing 1 at the proximal end of the consumable 31.

The second consumable 32 is a heated liquid containing reservoir. An aerosol-forming liquid is contained in a hollow tubular shaped reservoir. The liquid is supplied by a wick material to a coil heater 60, where the liquid is heated and evaporated. In a central conduit 301 of the consumables, the evaporated liquid is led out of the receiving chamber.

Electrical contacts (not shown) in the first and second receiving chamber are in contact with electrical contacts of the first and second consumable 31, 32 for providing power to the mesh heater 64 in the first consumable 31 and/or to the coil heater 60 of the second consumable.

The third receiving chamber is provided with a heating element 63, for example a resistive heating element. The third consumable 33 is a shell filled with a solid tobacco material 311, for example shredded tobacco or homogenized tobacco material. The tobacco material 311 of the third consumable 33 is heated by the heating element 63.

In some example embodiments, including the example embodiments shown in FIG. 11, the device housing 1 comprises three airflow inlets in the bottom of the housing. Three individual air channels 501 lead from the airflow inlets to the distal ends of the three consumables. Thus an airflow 500 entering the device housing is directly guided to one consumable only, passes through the consumable and to an adult vaper drawing on the consumable. Each flow path, for example each airflow channel may be provided with a puff activation switch (also called a draw activation switch).

Figure 12:
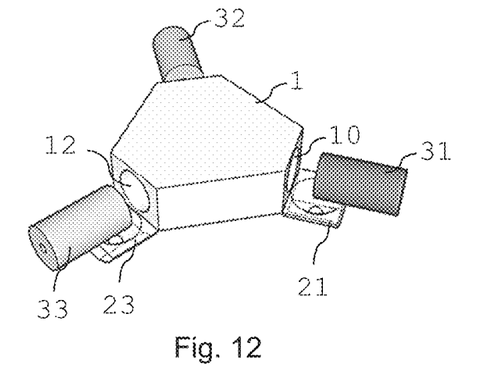
FIGS. 12, 13, and 14 show a device comprising three consumables and individual transparent mouthpieces, according to some example embodiments.
Figure 13:
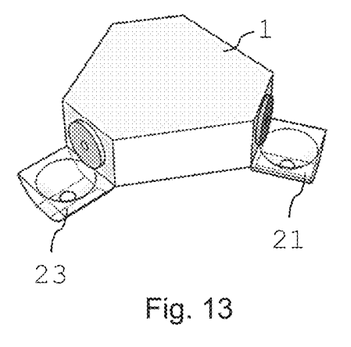
Figure 14:
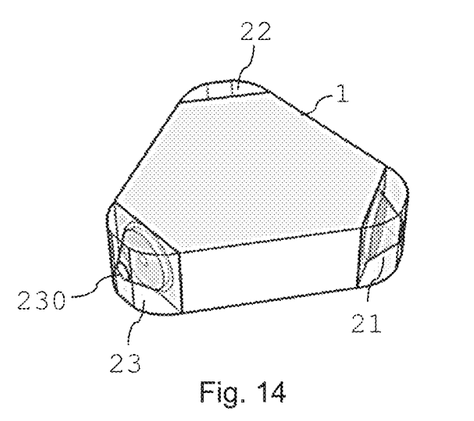

FIGS. 12, 13, and 14 show a device comprising three consumables and individual transparent mouthpieces, according to some example embodiments.

FIG. 12, FIG. 13 and FIG. 14 show a triangular-shaped device housing 1 with three consumables 31, 32, 33 and three mouthpieces 21, 22, 23. The housing is symmetric and the consumables are regularly arranged in a star-shaped manner in the device housing 1.

The mouthpieces are 21, 22, 23 are arranged at the three corners of the triangle forming the device housing 1. The mouthpieces 21, 22, 23 are connected to the device housing 1 with a hinge each and are made of a transparent material.

In FIG. 12 the mouthpieces are open and three tubular-shaped consumables are ready to be inserted into the three receiving chambers 10, 11, 12. FIG. 13 shows the consumables in an accommodated state. In FIG. 14 the device is shown with the mouthpieces 21, 22, 23 in a closed state and the device is ready for being used. The transparent material of the mouthpieces allows view onto the consumables arranged in the device housing. It may also be seen that the mouthpieces cover the proximal ends of the consumables (e.g., mouthpiece 23 covers the proximal end of the consumable 33) and guide respective airflows in respective funnels to the outlet openings in the mouthpieces (e.g., mouthpiece 23 may guide an airflow in a funnel to the outlet opening 230 in the mouthpiece 23).

Figure 15:
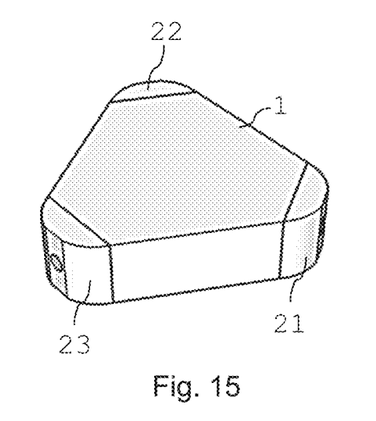
FIG. 15 shows the device of FIG. 12 with non-transparent mouthpieces, according to some example embodiments.

FIG. 15 shows the device of FIG. 12 with non-transparent mouthpieces, according to some example embodiments.

The device as shown in FIG. 14 may entirely be made of non-transparent material as shown in FIG. 15. View onto residuals possibly adhering to an inside of the mouthpieces may be excluded by using non-transparent materials for the mouthpieces 21, 22, 23.

Figure 16:
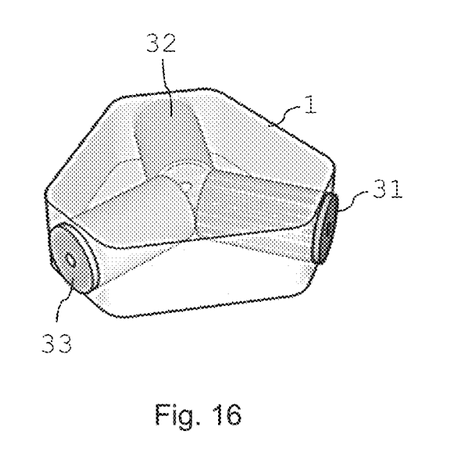
FIG. 16 shows a transparent device housing of a device comprising three consumables, according to some example embodiments.

FIG. 16 shows a transparent device housing of a device comprising three consumables, according to some example embodiments.

FIG. 16 shows a triangular-shaped device housing 1 made of transparent material. The device housing 1 allows view onto the star-shaped arrangement of the consumables 31, 32, 33 arranged in the housing. The longitudinal axis of the consumables each include an angle of 120 degree.

Figure 17:
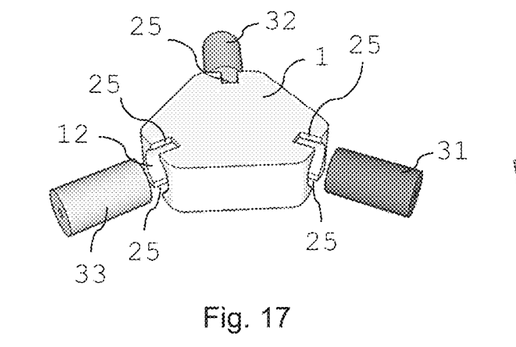
FIG. 17 shows a triangular-shaped device comprising cutouts for access to the three consumables in the device, according to some example embodiments.

FIG. 17 shows a triangular-shaped device comprising cutouts for access to the three consumables in the device, according to some example embodiments.

FIG. 17 shows a triangular-shaped housing 1, wherein each of the receiving chambers 12 are provided with two opposite and longitudinally arranged slits 25. The three receiving chambers as well as the consumables 31, 32, 33 are arranged in the form of a star in the device housing 1.

Figure 18:
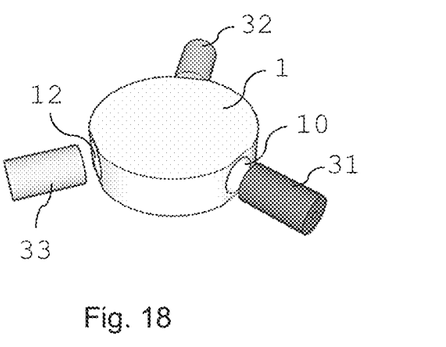
FIG. 18 shows a disc-shaped device housing according to some example embodiments.

FIG. 18 shows a disc-shaped device housing according to some example embodiments.

The device housing 1 of the device shown in FIG. 18 has a disc shape with a circular circumference. The receiving chambers 10, 12 as well as the consumables are arranged in a star-like manner in the device housing 1. The longitudinal axis of the consumables 31, 32, 33 each include an angle of 120 degree.

Figure 19:
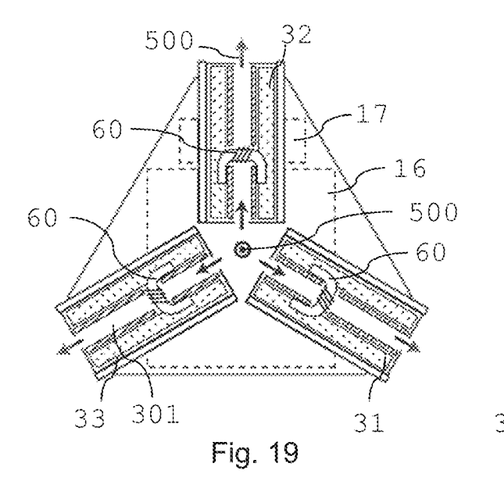
FIG. 19 shows a cross section through a triangular-shaped device and an airflow through a common kind of consumables, according to some example embodiments.
Figure 20:
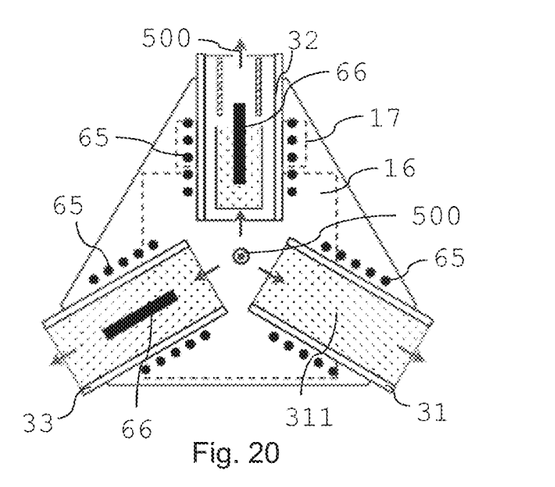
FIGS. 20 and 21 show cross sections through triangular-shaped devices and an airflow through different types of consumables, according to some example embodiments.
Figure 21:
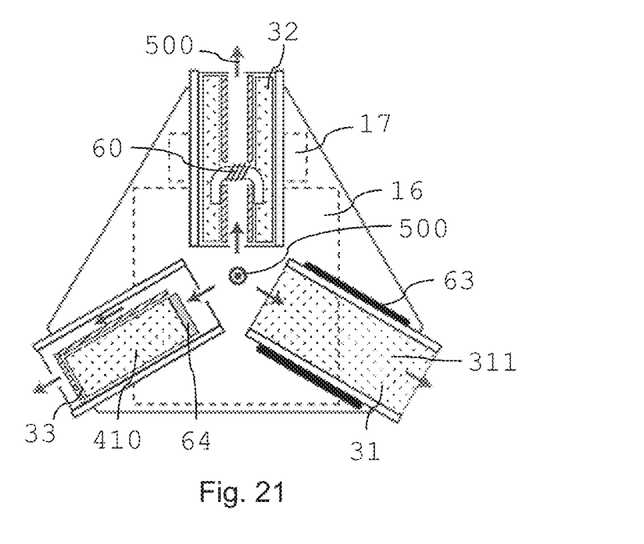

FIG. 19 shows a cross section through a triangular-shaped device and an airflow through a common kind of consumables, according to some example embodiments. FIGS. 20 and 21 show cross sections through triangular-shaped devices and an airflow through different types of consumables, according to some example embodiments.

FIG. 19, FIG. 20 and FIG. 21 schematically show cross sections through aerosol-generating devices comprising three consumables 31, 32, 33 arranged in a regular star shape, for example embodiments of the devices as shown in FIGS. 12 to 17.

FIGS. 19 to 21 also show examples of airflows passing through the three consumables.

The device housing 1 comprise three receiving chambers (not shown) arranged in a star shape including an angle of 120 degree between each of the longitudinal axis of the receiving chambers. The device housing 1 also comprises three consumables 31, 32, 33 accommodated in the receiving chambers, a power source 16 and a controller 17 for controlling the power source and the device.

The device housing is provided with a central air inlet arranged in the center of the triangle on one large side of the device housing 1. An airflow 500 entering the device through this central air inlet passes radially into the direction of a corner of the triangle. Thereby the airflow passes through a consumable accommodated in the receiving chamber.

The airflow 500 may passes through a mouthpiece aligned with the respective consumable and receiving chamber (not shown).

In some example embodiments, including the example embodiments shown in FIGS. 19 to 21, power source 16 and controller 17 are basically arranged in a layer parallel to the receiving chambers and parallel to one large side of the device housing 1.

In FIG. 19, the three consumables are of a same type. All three consumables are a heated liquid containing reservoir. An aerosol-forming liquid is contained in a hollow tubular shaped reservoir. The liquid is supplied by a wick material to a coil heater 60, where the liquid is heated and evaporated. In a central conduit 301 of the consumables, the evaporated liquid is led out of the receiving chamber. The three cartridges preferably differ in terms of at least one of nicotine strength, flavor or vapor volume.

The receiving chambers comprise electrical contacts (not shown) for providing power from the power source 16 to the coil heaters 60 of the consumables 31, 32, 33.

The controller 17 of the device is configured to provide required power to the coil heater 60 of the consumables.

In FIG. 20, the device housing 1 comprises induction heating. In the receiving chamber side walls an induction coil 65 is arranged. Each induction coil 65 preferably surrounds the respective receiving chamber.

The consumables 32, 33 arranged in the second and third receiving chamber comprise a susceptor 66, for example a ferrous material, for heating an aerosol-forming substrate in the consumable. The second consumable 32 of FIG. 20 is depicted as containing liquid that is wicked and evaporated by the heated susceptor. The first and third consumables 31, 33 of FIG. 20 are depicted as a shell, preferably tubular shaped, filled with a solid tobacco material 311, for example shredded tobacco or homogenized tobacco material. The tobacco material 311 of the third consumable 33 is heated by the susceptor 66 arranged in the tobacco material. The tobacco material 311 of the third consumable 33 is not heated.

In the device of FIG. 21, three different types of consumables 31, 32, 33 are arranged in the device housing 1. A third consumable 33 comprises aerosol-forming liquid in a storage portion 410 of the consumable 33. The storage portion 410 comprises an open end, where a mesh heater 64 or other fluid permeable heater, is arranged over the open end. The liquid is heated by the heated mesh heater 64. The consumable is positioned in the receiving chamber such that air passes the mesh heater 64, thereby pick up evaporated substances, passes along the exterior of the storage portion 410 and out of the device housing 1 at the proximal end of the consumable 33.

The second consumable 32 is a heated liquid containing reservoir. An aerosol-forming liquid is contained in a hollow tubular shaped reservoir. The liquid is supplied by a wick material to a coil heater 60, where the liquid is heated and evaporated. In a central conduit of the consumable, the evaporated liquid is led out of the receiving chamber.

Electrical contacts (not shown) in the third and second receiving chambers are in contact with electrical contacts of the third and second consumable 33, 32 for providing power to the mesh heater 64 in the third consumable 33 and to the coil heater 60 of the second consumable 32.

The first receiving chamber is provided with a heating element 63, for example a resistive heating element. The first consumable 31 is a shell filled with a solid tobacco material 311, for example shredded tobacco or homogenized tobacco material. The tobacco material 311 of the first consumable 33 is heated by the heating element 63.

A detection system in the devices may be integrated or connected to the controller 17 and may recognize the type of consumable accommodated in the receiving chambers. For example, next to an electronic recognition, a touch sensor may be provided in the receiving chamber to generate signals that may be processed by a processor included in the detection system to enable the processor to determine ("recognize") the presence or absence of a consumable based on processing one or more signals received at the processor from the touch sensor.

The invention claimed is:

1. An aerosol-generating system comprising:
   an aerosol-generating device, the aerosol-generating device including a device housing, the device housing including at least two receiving chambers;
   at least two consumables including an aerosol-forming substrate, each consumable of the at least two consumables accommodated in a separate receiving chamber of the at least two receiving chambers; and
   at least two mouthpieces, each mouthpiece of the at least two mouthpieces aligned with a separate consumable of the at least two consumables,
   wherein the aerosol-generating device is configured to isolate airflows through separate, respective mouthpieces of the at least two mouthpieces.

2. The aerosol-generating system according to claim 1, wherein at least one mouthpiece of the at least two mouthpieces is included in the aerosol-generating device.

3. The aerosol-generating system according to claim 1, further comprising:
   a mouthpiece assembly, the mouthpiece assembly including the at least two mouthpieces.

4. The aerosol-generating system according to claim 1, wherein at least one consumable of the at least two consumables includes one mouthpiece of the at least two mouthpieces.

5. The aerosol-generating system according to claim 1, wherein one consumable of the at least two consumables includes an aerosol-forming liquid and a heating element, the heating element configured to heat the aerosol-forming liquid.

6. The aerosol-generating system according to claim 1, wherein one consumable of the at least two consumables includes a solid tobacco material.

7. The aerosol-generating system according to claim 1, wherein the aerosol-generating device is a handheld device.

8. An aerosol-generating device, comprising:
   a device housing including at least two receiving chambers, each receiving chamber of the at least two receiving chambers configured to receive and accommodate a separate consumable, each receiving chamber of the at least two receiving chambers including one of
      a heating element configured to heat the separate consumable accommodated in the receiving chamber, electrical contacts connectable to an external heating element of the separate consumable accommodated in the receiving chamber, the electrical contacts configured to heat the separate consumable accommodated in the receiving chamber, or an induction coil configured to heat a susceptor material provided in the aerosol-generating device or in the separate consumable accommodated in the receiving chamber.

9. The aerosol-generating device according to claim 8, further comprising:

at least two mouthpieces, wherein each mouthpiece of the at least two mouthpieces covers a receiving opening of a receiving chamber of the at least two receiving chambers based on the mouthpiece being mounted to the device housing.

10. The aerosol-generating device according to claim 9, wherein each mouthpiece is connected to the device housing via a hinge.

11. The aerosol-generating device according to claim 9, wherein each mouthpiece of the at least two mouthpieces includes an inlet opening and an outlet opening, and the inlet opening is aligned with a receiving opening of a separate receiving chamber of the at least two receiving chambers.

12. The aerosol-generating device according to claim 9, wherein the aerosol-generating device is configured to isolate airflows through separate, respective mouthpieces of the at least two mouthpieces.

13. The aerosol-generating device according to claim 9, further comprising:

a mouthpiece assembly, the mouthpiece assembly including the at least two mouthpieces.

14. The aerosol-generating device according to claim 8, wherein at least one receiving chamber of the at least two receiving chambers includes a heating element, and the heating element is in a receiving chamber wall or extends into the at least one receiving chamber.

15. The aerosol-generating device according to claim 8, wherein each receiving chamber of the at least two receiving chambers is elongate and has a longitudinal axis, and the at least two receiving chambers extend in parallel in the device housing such that the longitudinal axes of the at least two receiving chambers extend in parallel.

16. The aerosol-generating device according to claim 8, wherein each receiving chamber of the at least two receiving chambers is elongate and has a longitudinal axis, and the longitudinal axes of the at least two receiving chambers extend in different directions within the device housing.

17. The aerosol-generating device according to claim 8, wherein the device housing includes three or more receiving chambers configured to receive and accommodate three or more consumables, the three or more receiving chambers including the at least two receiving chambers.

18. The aerosol-generating device according to claim 17, wherein each receiving chamber of the three or more receiving chambers is elongate and has a longitudinal axis, and the longitudinal axes of the three or more receiving chambers extend in different directions and the longitudinal axes of adjacent receiving chambers intersect at an alignment angle, the alignment angles between the longitudinal axes of all of the adjacent receiving chambers being substantially equal.

19. The aerosol-generating device according to claim 8, wherein the aerosol-generating device is a handheld device.

* * * * *